United States Patent [19]

Hoeffkes et al.

[11] Patent Number: 4,784,801
[45] Date of Patent: Nov. 15, 1988

[54] HAIR TREATMENT PREPARATIONS

[75] Inventors: Horst Hoeffkes, Duesseldorf-Hellerhof; Fritz Lange, Essen; Karl Giede, Hilden, all of Fed. Rep. of Germany

[73] Assignee: Henkel Kommanditgesellschaft auf Aktien, Duesseldorf, Fed. Rep. of Germany

[21] Appl. No.: 69,790

[22] Filed: Jul. 2, 1987

[30] Foreign Application Priority Data

Jul. 4, 1986 [DE] Fed. Rep. of Germany ....... 3622439

[51] Int. Cl.$^4$ ........................... C11D 1/14; C11D 1/12
[52] U.S. Cl. ................................ 252/554; 252/174.21; 252/DIG. 5; 252/DIG. 13; 252/DIG. 14; 424/70
[58] Field of Search .......... 252/554, 174.21, DIG. 5, DIG. 13, 252/DIG. 14; 424/70

[56] References Cited

PUBLICATIONS

Jacobs, R. A., "Novel Anionic Sulfonates" Soaps/Cosmetics/Chemical Specialties, Feb., 1987, pp. 41-42,57.

Primary Examiner—Paul Lieberman
Assistant Examiner—Kathleen Markowski
Attorney, Agent, or Firm—Ernest G. Szoke; Henry E. Millson, Jr.; Wayne C. Jaeschke

[57] ABSTRACT

Aqueous hair treatment preparations containing as anionic surfactant an alkylether sulfonate corresponding to the following formula

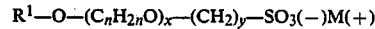

$$R^1-O-(C_nH_{2n}O)_x-(CH_2)_y-SO_3(-)M(+)$$

in which $R^1$ is a $C_8$–$C_{18}$ alkyl group, $n=2$ or 3, $x=0$ to 20, $y=1$ to 3 and $M(+)$ is an alkali metal ion. Alkylether sulfonates such as these show high foaming power, are easy to thicken and are stable to hydrolysis in acidic medium. They can be prepared by reaction of corresponding alkylether sulfates with sodium sulfite in aqueous solution and extraction from the reaction mixture with a saturated $C_4$–$C_6$ alcohol.

9 Claims, No Drawings

HAIR TREATMENT PREPARATIONS

BACKGROUND OF THE INVENTION

1. Field of the Invention

This invention relates to aqueous cosmetic hair treatment preparations containing an alkylether sulfonate anionic surfactant and preferably having an acidic pH value.

2. Statement of Related Art

Many aqueous hair treatment preparations contain surfactants to obtain better wetting of the hair, emulsification or dispersion of water-soluble components, more uniform distribution of the components on the hair, or to obtain a foaming and washing effect. Among the surfactants used, anionic surfactants are the most important by virtue of their good foaming and washing power and their good wetting and dispersing action. Alkylether sulfates in particular have acquired considerable significance by virtue of these favorable performance properties and because they can be heavily thickened, even in dilute aqueous solution, by addition of electrolytes. However, they are attended by the disadvantage that they undergo hydrolysis during prolonged storage, particularly at pH values below 5, by a reaction which is autocatalytically accelerated once it has started through the formation of sulfuric acid. Known hydrolysis-stable surfactants, for example nonionic ethylene oxide adducts, are not sufficiently foam-forming; others, for example the anionic alkylbenzene sulfonates, are not sufficiently compatible with the skin for cosmetic applications and yet others, for example the alkane sulfonates and α-olefin sulfonates, cannot be sufficiently thickened with electrolytes in aqueous solution, which is a disadvantage where they are to be used for example in shampoos.

Accordingly, there is a particular need for cosmetic hair treatment preparations which contain an hydrolysis-stable surfactant having favorable performance properties, particularly foam power, compatibility with the skin and thickenability in aqueous solution.

DESCRIPTION OF THE INVENTION

Other than in the operating examples, or where otherwise indicated, all numbers expressing quantities of ingredients or reaction conditions used herein are to be understood as modified in all instances by the term "about".

It has now been found that alkylether sulfonates, particularly those corresponding to formula (I) below, are especially suitable for the production of hair treatment preparations of the type discussed above.

The present invention relates to aqueous cosmetic hair treatment preparations containing an anionic surfactant, wherein the anionic surfactant is an alkylether sulfonate corresponding to the following general formula $$R^1-O-(C_nH_{2n}O)_x-(CH_2)_y-SO_3^{(-)}M^{(+)} \quad (I)$$

in which $R^1$ is a $C_8$–$C_{18}$ alkyl group, $n=2$ or 3, $x=0$ to 20, $y=1$ to 3 and $M^{(-)}$ is an alkali metal ion. The alkylether sulfonate is preferably present as the sole anionic surfactant in a quantity of from 1 to 20% by weight, based on the preparation as a whole, where the hair treatment preparation is acidic and has a pH value of from 1 to 5.

Alkylether sulfonates suitable for the hair treatment preparations of the invention are known from the literature and may be obtained, for example, by any of the following methods:

(a) Reaction of alkyl polyglycol ether chlorides corresponding to the following general formula $$R^1-O-(C_nH_{2n}O)_x-(CH_2)_2-Cl$$

with sodium sulfite, for example, in accordance with U.S. Pat. No. 4,283,321 or U.S. Pat. No. 4,329,268.

(b) Reaction of alkyl polyglycol ether sulfates corresponding to the following general formula $$R^1-O-(C_nH_{2n}O)_x-(CH_2)_2-OSO_3^{(-)}Na^{(+)}$$

with sodium sulfite, for example, in accordance with U.S. Pat. No. 3,827,497.

(c) Reaction of alkyl polyglycol ether alcoholates, for example corresponding to the following formula $$R^1-O-(C_nH_{2n}O)_xNa$$

with propane sultone, for example, in accordance with German published application No. 27 24 442, or with 2-bromoethane sulfonic acids or sodium isethionate.

(d) Reaction of alkyl polyglycol ethers corresponding to the following formula $$R^1-O-(C_nH_{2n}O)_x-H$$

with allyl halide to form the corresponding allyl ether
$$R^1-O-(C_nH_{2n}O)_x-CH_2CH=CH_2$$

and reaction of this allyl ether with sodium bisulfite, for example in accordance with European patent application No. 64 384.

In the above formulae, $R^1$, n and x have the same meanings as in formula I.

The alkylether sulfonates prepared by the processes described above are generally obtained in the form of the sodium salt. However, they may also be obtained in the form of the potassium salt (for example where potassium sulfite is used in the reaction according to (a) or (b)). However, lithium, magnesium, monoethanolammonium, triethanolammonium and isopropanolammonium salts of the alkylether sulfonates, which can be obtained in known manner from the alkali metal salts, are also suitable for the hair treatment preparations according to the invention.

The alkylether sulfonates corresponding to general formula I in which $y=2$ and $M^{(+)}$ is a sodium ion are preferably used. Alkylether sulfonates such as these can be obtained particularly elegantly by method (b) from alkylether sulfates by reaction with sodium sulfite in aqueous solution under pressure at 150° to 200° C. Reaction conditions have been found which facilitate substantial reaction to the alkylether sulfonates and subsequent separation of the surfactant from the sodium sulfate and excess sodium sulfite.

Accordingly, the present invention also relates to a process for the production of alkylether sulfonates corresponding to formula I, in which $R^1$ is a $C_8$–$C_{18}$ alkyl group, $n=2$ or 3, $x=0$ to 20, $y=2$ and $M^{(+)}$ is a sodium ion, by reaction of an alkylether sulfate corresponding to the formula $R^1-O(C_nH_{2n}O)_x-(CH_2)_2-OSO_3^{(-)}Na^{(+)}$ with sulfite, wherein the reaction is carried out under pressure at 150°–250° C. in aqueous solution with 1.5–4.0 moles of sodium sulfite per mole of alkylether sulfate and the reaction product is extracted from the reaction mixture with a saturated $C_4$-$C_6$ alcohol.

n-Butanol and n-hexanol are particularly suitable for extraction of the alkylether sulfonate.

Hydrolysis of the alkylether sulfate occurs to a relatively minor extent as a secondary reaction. The unsulfated components thus formed are extracted from the aqueous solution together with the alkylether sulfonate. The alkylether sulfonates prepared by the process according to the invention thus contain about 10 to 30% by weight of these unsulfated components.

The hair treatment preparations of the invention are distinguished by performance properties comparable with those of hair treatment preparations produced with alkylether sulfates and, in particular, by good foaming properties, good thickenability and good compatibility with the skin and mucous membrane. In addition, the products are stable in storage even at low pH-values.

In the production of these hair treatment preparations, the typical auxiliaries and additives or those required for the particular preparation can be used in addition to the alkylether sulfonates without any problems arising through inadequate compatibility with the alkylether sulfonates. Thus, shampoos may contain other hydrolysis-stable surfactants, for example nonionic alkyl polyglycol ethers containing from 10 to 18 C-atoms in the alkyl group and from 6 to 20 glycol ether groups or alkylphenol polyglycol ethers containing from 8 to 12 C-atoms in the alkyl group and from 8 to 20 glycol ether groups.

Hair treatment preparations according to the invention preferably contain the alkylether sulfonates of formula I as the sole anionic surfactant in a quantity of from 1 to 20% by weight, based on the preparations as a whole. The pH-value of hair treatment preparations such as these is preferably in the range of from 1 to 5.

Where the hair treatment preparations according to the invention are shampoos or shower preparations which have to form a thick lather unaffected by fats, the additional presence of ampholytic or zwitterionic surfactants or amine oxide surfactants is advisable, preferably in a quantity of from 10 to 50% by weight, based on the weight of the anionic surfactant.

Suitable ampholytic surfactants are, for example, N-alkyl-$\beta$-aminopropionic acids, N-alkyl-$\beta$-iminodipropionic acids, N-hydroxyethyl-N-alkylamidopropyl glycine, N-alkyl taurines, all containing from 8 to 18 carbon atoms in the alkyl group. Suitable zwitter-ionic surfactants are, for example, betaine surfactants, such as N-alkyl-N,N-dimethyl glycine, N-alkylamidopropyl-N,N-dimethyl glycine, in each case containing from 8 to 18 C-atoms in the alkyl group. Suitable amine oxide surfactants are, for example, N-cocosamidopropyl-N,N-dimethylamine oxide or N-cocosalkyl-N,N-di-(2-hydroxy)-ethylamine oxide.

The alkylether sulfonates corresponding to formula I are particularly suitable as base surfactants for acidic caring shampoos for permanently waved and colored hair and for the production of aqueous hair treatment preparations containing from 1 to 10% by weight hydrogen peroxide, of the type used for exaple as developers for oxidation hair dyes or as acidic setting solutions after permanent waving. Solutions such as these are preferably mildly acidified, for example through an addition of citric acid, tartaric acid, phosphoric acid or organophosphonic acids.

In addition to the characteristic alkylether sulfonates and the components mentioned above, the hair treatment preparations of the invention may contain any of the constituents typical of such preparations, including in particular nonionic, ampholytic, zwitterionic and amine oxide surfactants and also perfumes, cosmetic oil and fat components, fatty alcohols, waxes, buffer salts, preservatives and dyes.

The following Examples are intended to illustrate the invention without limiting it in any way.

EXAMPLES

1. Production Examples

1.1 Production of alkyl ($C_{12}$-$C_{14}$)+2EO sulfonate, Na salt 10 kg of a 70% aqueous alkylether sulfate-sodium salt paste (base lauryl-myristyl (70:30) alcohol+2 moles ethylene oxide), 7.7 kg sodium sulfite and 26.6 kg water were heated for 3 hours to 200° C. in an autoclave. After cooling to 25° C., the reaction mixture was extracted 3 times with n-butanol and the n-butanol distilled off from the extract. 6.0 kg of a wax-like solid product containing 1.83 mvals/g anionic surfactant (as determined by DGF-Einheitsmethode H-III-10)* and 18.4% by weight unsulfated components were obtained.

1.2 Production of alkyl ($C_{12}$-$C_{14}$)+3.6EO sulfonate, Na salt

As in Example 1, 20.3 kg of a 30% aqueous alkylether sulfate-sodium salt solution (base lauryl-myristyl (50:50) alcohol+3.6 moles ethylene oxide), 4.9 kg sodium sulfite and 14.8 kg water were heated for 3 hours to 200° C. After working up, a wax-like solid product containing 1.63 mvals/g anionic surfactant (as determined by DGF-Einheitsmethode H-III-10)* and 20% by weight unsulfated components was obtained in a quantity of 5.6 kg.

1.3 Production of alkyl—($C_{12}$-$C_{15}$)+12EO sulfonate, Na salt

As in Example 1, 990 g of a 30% aqueous solution of an alkylether sulfate-sodium salt (base $C_{12}$-$C_{15}$ oxoalcohol+12 moles ethylene oxide), 160 g sodium sulfite and 350 g water were heated for 3 hours to 200° C.

After working-up, a wax-like solid product containing 0.844. mvals/g anionic surfactant (as determined by DGF-Einheitsmethode H-III-10)* was obtained in a quantity of 250.7 g.

2. Application Examples

2.1 Acidic shampoo

| | |
|---|---|
| Alkylether sulfonate of Example 1.1 | 10% by weight |
| $C_{12}$-$C_{18}$ acylaminopropyl dimethyl ammonium glycinate | 3% by weight |
| Perfume oil | 0.2% by weight |
| Bronidox( TM ) L (preservative)** | 0.2% by weight |
| Citric acid | to pH 3 |
| Water | ad 100% by weight |

2.2 Acidic permanent-wave setting solution

| | |
|---|---|
| Alkylether sulfonate of Example 1.1 | 4% by weight |
| Citric acid | 0.5% by weight |
| Hydrogen peroxide, 30% solution | 5% by weight |
| Sodium pyrophosphate | 0.5% by weight |

-continued

| | |
|---|---|
| Perfume oil | 0.3% by weight |
| Water | ad 100% by weight |

*Determination of the anionic surfactant content by DGF-Einheitsmethode H-III-10 was carried out by the so-called two-phase titration method. The hydrolysable components of alkylether sulfate were removed beforehand by acidic hydrolysis (2nHCl).
**Solution of 10% by weight of 5-bromo-5-nitro-1.3-dioxan in 1.2-propylenglycol (Henkel KGaA, Düsseldorf, Germany).

2.3 Developer dispersion for oxidation hair dyes

| | |
|---|---|
| Cetyl alcohol | 2% by weight |
| Alkylether sulfonate of Example 1.3 | 3% by weight |
| Fatty alcohol (C$_{12}$-C$_{14}$) + 3 moles ethylene oxide | 2% by weight |
| Hydrogen peroxide (30% solution) | 20% by weight |
| Hydroxyethane diphosphonic acid | 0.5% by weight |
| Water | ad 100% by weight |

We claim:

1. In an aqueous hair treatment composition containing an anionic surfactant, the improvement wherein the anionic surfactant is an alkylether sulfonate of the formula $$R^1-O-(C_nH_{2n}O)_x-(CH_2)_y-SO_3^{(-)}M^{(+)} \qquad (I)$$

in which $R^1$ is a $C_8$-$C_{18}$ alkyl group, $n=2$ or 3, $x=0$ to 20, $y=1$ to 3 and $M^{(+)}$ is an alkali metal ion.

2. The hair treatment composition of claim 1 wherein, in the alkylether sulfonate of formula I, $Y=2$ and $M^{(+)}$ is the sodium ion.

3. The hair treatment composition of claim 1 wherein the alkylether sulfonate of formula I is the only anionic surfactant in the composition and is present in a quantity of from about 1 to about 20% by weight, based on the weight of the composition.

4. The hair treatment composition of claim 1, wherein the composition has a pH in the range of from about 1 to about 5.

5. The hair treatment composition of claim 3, wherein the composition has a pH in the range of from about 1 to about 5.

6. The hair treatment composition of claim 1, wherein the composition also contains from about 10 to about 50% by weight, based on the weight of the anionic surfactant, of an amphoteric or zwitter-ionic surfactant.

7. The hair treatment composition of claim 1 wherein the composition also contains from about 1 to about 10% by weight of hydrogen peroxide.

8. The hair treatment composition of claim 5 wherein the composition also contains from about 1 to about 10% by weight of hydrogen peroxide.

9. A process for the preparation of an alkylether sulfonate of the formula:

$$R^1-O(C_nH_{2n}O)_x-(CH_2)_y-SO_3^{(-)}M^{(+)} \qquad (I)$$

in which $R^1$ is a $C_8$-$C_{18}$ alkyl group, $n=2$ or 3, $x=0$ to 20, $y=2$ and $M^{(+)}$ is the sodium ion, comprising the steps of: A. reacting an alkylether sulfate of the formula $$R^1-O(C_nH_{2n}O)_x-(CH_2)_2-O-SO_3^{(-)}Na^{(+)}$$

with sodium sulfite under pressure at a temperature in the range of from about 150° to about 250° C. in aqueous solution with from about 1.4 to about 4.0 moles of sodium sulfite per mole alkylether sulfate, and B. extracting the alkylether sulfonate of formula I from the reaction mixture with a saturated $C_4$-$C_6$ alcohol.

* * * * *